United States Patent [19]
Gheysen

[11] Patent Number: 6,036,959
[45] Date of Patent: *Mar. 14, 2000

[54] HCMV/HSV FUSION GLYCOPROTEINS

[75] Inventor: Dirk Richard Gheysen, Overijse, Belgium

[73] Assignee: SmithKline Beecham Biologicals (s.a.), Belgium

[ * ] Notice: This patent is subject to a terminal disclaimer.

[21] Appl. No.: 08/997,211

[22] Filed: Dec. 23, 1997

Related U.S. Application Data

[62] Division of application No. 08/443,642, May 18, 1995, Pat. No. 5,739,292.

[30] Foreign Application Priority Data

May 18, 1994 [GB] United Kingdom ............... 9409962

[51] Int. Cl.[7] ..................... A61K 39/00; A61K 39/245; C12P 21/06; C07K 1/00
[52] U.S. Cl. ..................... 424/202.1; 424/185.1; 424/184.1; 424/192.1; 424/230.1; 424/186.1; 530/395; 435/69.3; 435/69.1; 435/69.7; 536/23.5
[58] Field of Search ............... 424/185.1, 184.1, 424/192.1, 230.1, 186.1, 202.1; 530/395; 435/69.3, 69.1, 69.7; 536/23.5

[56] References Cited

U.S. PATENT DOCUMENTS 5,739,292  4/1998  Gheysen .................. 530/395

FOREIGN PATENT DOCUMENTS

WO 88/02634  4/1988  WIPO .................. A61K 39/245
WO 89/07143  10/1989  WIPO .................. C12N 15/00

OTHER PUBLICATIONS

Aurelian L., "Herpes Simplex Viruses", In: Encyclopedia of Virology, vol. 2, Webster & Granoff, A., eds., Academic Press, New York, pp. 587–593, 1994.
Cranage et al. The EMBO Journal 5(11): 3057–3063, 1986.
Britt et al. Journal of Infectious Diseases 171:18–25, 1995.
Curtsinger et al. Journal of General Virology 75: 301–307, 1994.
Flexner, et al., "Successful vaccination with a polyvalent live vector despite existing immunity to an expressed antigen", *Nature*, 335, No. 6187, pp. 259–262 (1988).
Cranage, et al., "Identification of the human cytomegalovirus glycoprotein B gene and induction of neutralizing antibodies via its expression in recombinant vaccinia virus", *The Embo Journal*, 5, No. 11, pp. 3057–3063 (1986).
Forrester, et al., "Construction and Properties of a Mutant of Herpes Simplex Virus Type 1 with Glycoprotein H Coding Sequences Deleted", *J. Virol.*, 66, No. 1, pp. 341–348 (1992).

*Primary Examiner*—Donna C. Wortman
*Assistant Examiner*—Mary K Zeman
*Attorney, Agent, or Firm*—Kirk Baumeister; William T. King; Chales M. Kinzig

[57] ABSTRACT

A fusion protein comprising a portion of a glycoprotein of HCMV fused to a portion of a glycoprotein of HSV is described.

13 Claims, 2 Drawing Sheets

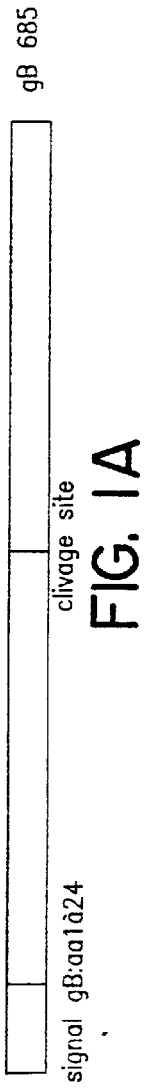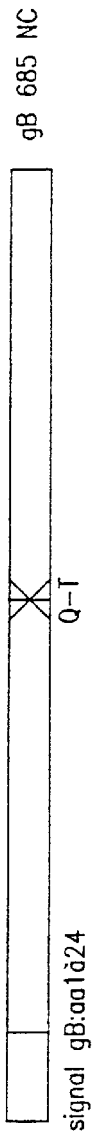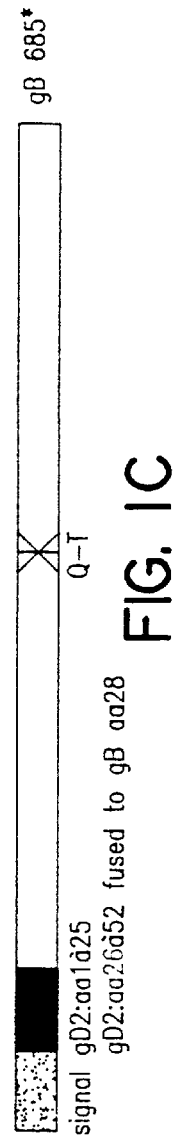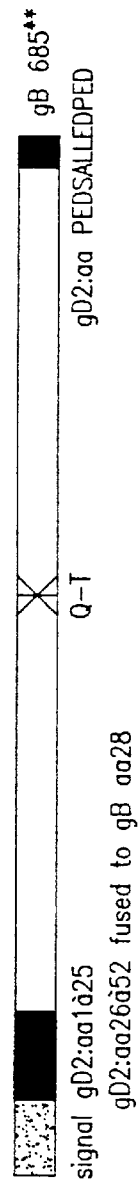

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Human cytomegalovirus
        (B) STRAIN: AD169
        (C) INDIVIDUAL ISOLATE: Dir 268

(xi) SEQUENCE DESCRIPTION: SEQ ID NO:1:

GGACCCAAAC AAGTACGAGT G                           21

(2) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:2:

```
CGCTGGTGAA AGTAAAAGAT GC                                                    22

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:3:

GTACTTGTTT GGGTCCTATG                                                       20

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:4:

CCGCTGTTGA GATCCAGTTC G                                                     21

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:5:

GCCTCAAGAT CTTCATCGCC GGGAACTCG                                             29

(2) INFORMATION FOR SEQ ID NO:6:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (xi) SEQUENCE DESCRIPTION: SEQ ID NO:6:

TAGCTCTAGA TTAATCCTCG GGATCCTCTA AGAGGGCCGA GTCCTCGGGG GAATTCGC             58

(2) INFORMATION FOR SEQ ID NO:7:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Asp Glu Pro Asp Glu Leu Leu Ala Ser Asp Glu Pro
 1               5                  10

(2) INFORMATION FOR SEQ ID NO:8:

(i) SEQUENCE CHARACTERISTICS:
        (A) LENGTH: 12 amino acids
        (B) TYPE: amino acid
        (C) STRANDEDNESS: single
        (D) TOPOLOGY: linear
```

-continued (ii) MOLECULE TYPE: peptide (xi) SEQUENCE DESCRIPTION: SEQ ID NO:8:

```
Pro Glu Asp Ser Ala Leu Leu Glu Asp Pro Glu Asp
 1               5                  10
```

HCMV/HSV FUSION GLYCOPROTEINS

RELATED APPLICATIONS

This application is a divisional of U.S. Ser. No. 08/443,642, filed on May 18, 1995. This application claims priority under 35 U.S.C. §119 to GB 9409962.9 filed May 18, 1994.

The present invention relates to recombinant cytomezalovirus proteins, more particularly to fusion proteins comprising a portion of a human cytomegalovirus (HCMV) protein and a portion of a protein from herpes simplex virus (HSV) and their expression in eukarvotic cells. The invention further relates to methods of constructing and expressing the said fusion proteins intermediates for use therein and recombinant proteins which may be obtained from the intermediates. Recombinant proteins of the invention have potential utility in the development of vaccines for the prevention of HCMV infection and/or HSV infection.

HCMV is human DNA virus belonging to the family of herpes viruses. In common with other herpetic viruses (such as Herpes Simplex Virus (HSV) Varicella Zoster Virus (VZV)) HCMV is made up of a DNA core, an outer capsid and covered by a lipid membrane which incorporates virus specific glycoproteins.

Human cytomegalavirus is endemic in most parts of the world. Primary infection however normally results in subclinical disease after which the virus becomes latent retaining the capacity to reactivate at any time. Among two populations, HCMV is however responsible for serious medical conditions. HCMV is a major cause of congenital defects in new borns. Also associated with infection in such infants, are hearing loss, and poor intellectual performance. The second population at risk are immunocompromised patients such as those suffering from HIV infection and those patients undergoing transplantations. In this situation the virus becomes an opportunistic pathogen and causes severe disease with high morbidity and mortality. The clinical disease causes a variety of symptoms including fever, hepatitis. pneumonitis, and infectious mononucleosis.

This therefore explains the extensive efforts of those skilled in the art and the importance of studies dedicated to the biology of these viruses. However no efficient vaccine against HCMV is currently available.

Therefore there still exists a need for antigens which will effectively protect against challenge with the HCMV virus.

According to a first aspect of the present invention there is provided a fusion protein or an immunogenic derivative thereof comprising a portion of an HCMV glycoprotein fused to a portion of a glycoprotein of HSV.

By a portion of an HCMV glycoprotein is meant a part of the protein which contains at least one antigenic determinant capable of raising an immune response specific to HCMV. A preferred HCMV glycoprotein is gB.

By a portion of a glycoprotein of HSV is meant a part of the protein which contains at least the signal sequence of the glycoprotein and optionally additional parts of the protein which contain at least one antigenic determinant capable of raising an immune response specific to HSV and/or contain a sequence enhancing the secretion of the protein when suitably expressed. A preferred HSV glycoprotein is gD. in particular HSV type 2gD.

The gB protein of HCMV strain AD 169 contains 906 amino acid residues: amino acids 1 to 24 correspond to the signal peptide and residues 712 to 776 the membrane anchor domain. The molecule presents 19 potential sites for glycosylation. Used alone for immunization, the gB protein generates an immunune response which is insufficient to confer protection against a challenge with the virus.

The protein gD from herpes simplex virus (HSV) is composed of 394 amino acids: its membrane anchor domain occurs in the C-terminal end of the molecule, between amino acid residues 339 and 365.

Preferably the fusion is between an amino acid in the N-terminal part of a portion of the HCMV gB protein and an amino acid at the C terminus of a portion of the HSV gD protein.

Preferably both the HCMV gB protein and the HSV gD protein components of the fusion protein of the invention lack a membrane anchor domain.

Preferably the portion of the HCMV gB protein comprises a non-cleaveable form of HCMV gB. Suitably this is achieved by changing one or more amino acids at a cleavage site of the protein. Preferably this is by exchanging ARLT 458 and Arg 459 for Glu and Thr respectively. Such a non-cleaveable form of gB is novel and forms a further aspect of the invention. One advantage of having a non-cleaveable form of gB is that there is a greater secretion of the protein when suitably expressed.

Suitably the portion of the HSV protein comprises the signal sequence of gD2 and optionally amino acids 26 to 52 of gD2 and/or the sequence from gD2 which is PEDSALLEDPED (SEQ ID NO: 8) or functionally equivalent derivatives thereof which are slightly shorter or longer.

Preferably the portion of gD includes amino acids from the signal portion of gD2 (amino acids 1 to 25) and the amino acids residues 26–52 of HSV2 gD.

In one specific embodiment there is provided a fusion protein comprising amino acid residues 1–52 of the HSV gD protein fused to residues 28–686 of the HCMV gB protein (herein designated HCMV gB 685*).

Preferably further sequences from HSV gD can be added to the fusion protein, in particular at the C terminus of the HCMV gB protein.

In a further preferred embodiment the amino acid sequence PEDSALLEDPED, (SEQ ID NO: 8) which is derived from an internal gD2 sequence is included at the C terminal end of the protein HCMV gB 685* to produce the protein herein designated HCMV gB 685**. This amino acid sequence improves the secretion of the fusion protein when suitably expressed.

The proteins HCMV gB 685* and HCMV gB 685** in particular have been found to be useful for developing an HCMV vaccine.

Further preferred fusion proteins are as defined in the claims.

The fusion proteins of the present invention are immunogenic. The term immunogenic derivative as used herein encompasses any molecule which is a fusion protein which is immunologically reactive with antibodies raised to the fusion protein of the present invention or parts thereof or with antibodies recognising the HCMV gB protein, the HSV gD protein. the HCMV virus or the HSV virus, or which elicits antibodies recognizing the fusion protein, the HCMV gB protein, the HSV gD protein, the HCMV virus or the HSV virus. In particular immunogenic derivatives which are slightly longer or shorter than the fusion protein of the present invention may be used. Such derivatives may, for example, be prepared by substitution, addition, or rearrangement of amino acids or by chemical modifications thereof including those for enabling coupling of the fusion protein to other carrier proteins such as tetanus toxoid or Hepatitis B surface antigen. All such substitutions and modifications are generally well known to those skilled in the art of peptide chemistry.

Immunogenic fragments of the fusion protein which may be useful in the preparation of vaccines may be prepared by expression of the appropriate gene fragments or by peptide synthesis, for example using the Merrifield synthesis (The Peptides, Vol 2., Academic Press, New York, p3).

In a further aspect of the invention there is provided recombinant DNA encoding the fusion protein of the invention. The recombinant DNA of the invention may form part of a vector, for example a plasmid, especially an expression plasmid from which the fusion protein may be expressed. Such vectors also form part of the invention, as do host cells into which the vectors have been introduced.

In order to construct the DNA encoding a fusion protein according to the invention. cDNA containing the complete coding sequences of the HCMV gB and HSV gD proteins may be manipulated using standard techniques [see for example Maniatis T. et al Molecular Cloning, Cold Spring Harbor Laboratory, Cold Spring Harbor N.Y. (1982)] as further described hereinbelow.

In the course of carrying out the techniques described above recombinant DNA encoding fragments of the HCMV gB and HSV gD proteins may be obtained which further forms part of the present invention.

In particular DNA segments encoding a non-cleaveable form of HCMV gB the truncated protein HCMV gB (gB lacking the membrane anchor domain) and the truncated protein HSV gD (gD lacking the 5' membrane anchor domain) are important intermediates.

Vectors comprising such DNA, hosts transformed thereby and the truncated or hybrid proteins themselves, expressed as described hereinbelow all form part of the invention.

For expression of the proteins of the invention, plasmids may be constructed which are suitable either for transfer into vaccinia virus or transfection into Chinese Hamster Ovary (CHO) cells or Vero cells. Suitable expression vectors are described hereinbelow.

For expression in vaccinia a vaccinia transfer plasmid such as pULB 5213 which is a derivative of pSC11 (Chakrabati et. al. Molecular and Cellular Biology 5, 3403–3409, 1985) may be used. In one aspect the protein may be expressed under the control of the vaccinia $P_{7.5}$ promoter.

For expression in CHO-K1 cells a glutamine synthetase (GS) vector such as pEE14 may suitably be used so that the protein is expressed under the control of the major immediate early promoter of human cytomegalovirus (hCMV-MIE). Alternatively a vector which allows the expression of the coding module as a polycistronic transcript with the neo selection gene may suitably be used. In one preferred aspect the coding module is under the control of the Rous Sarcoma Long Terminal Repeat (LTR) promoter.

Preferably the plasmid for expression in CHO-K1 cells carries a GS expression cassette suitable for gene amplification using methionine sulphoximine (MSX). Alternatively the plasmid for expression in CHO-K1 cells carries a DHFR expression cassette suitable for gene amplification using methotrexate (MTX).

Preferably expression of the fusion proteins of the present invention is carried out in the presence of sodium butyrate and/or dimethyl sulphoxide (DMSO) which have been found to enhance gene expression.

In yet another aspect of the invention there is provided a vaccine composition comprising a fusion protein according to the invention in combination with a pharmaceutically acceptable carrier, a protein according to the invention for use in vaccinating a host and the use of a protein according to the invention in the preparation of a vaccine.

It is known that amino acids 1–23 of mature gD can elicit in animals a protective and neutralising response against a lethal challenge moreover this peptide when appropriately formulated can elicit a CTL response (Watari et al, reference in Example 2 below).

Accordingly the fusion proteins of the present invention which contain this peptide not only offer a protective response for HCMV infection but also offer a protective response for HSN infection thereby providing a novel bi-functional vaccine Optionally, and advantageously, the vaccine of the present invention is combined with other immunogens to afford a polyvalent vaccine. In a particularly preferred embodiment the fusion protein is combined with other subcomponents of HSV eg. gD.

In a particular aspect the invention further provides a vaccine composition comprising a protein according to the invention together with a suitable carrier or adjuvant.

Vaccine preparation is generally described in New Trends and Developments in Vaccines, edited by Voller et al, University Park Press, Baltimore, Md. U.S.A., 1978. Encapsulation within liposomes is described for example by Fullerton, U.S. Pat. No. 4,235,877.

In the vaccine of the present invention, an aqueous solution of the protein(s) can be used directly. Alternatively, the protein, with or without prior lyophilisation can be mixed, absorbed or adsorbed with any of the various known adjuvants. Such adjuvants include, but are not limited to, aluminium hydroxide, muramyl dipeptide and saponins such as Quil A. Particularly preferred adjuvants are MPL (monophosphoryl lipid A) and 3D-MPL (3 deacylated monophosphoryl lipid A) [U.S. Pat. No. 4,912,094]. A further preferred adjuvant is known as QS21 which can be obtained by the method disclosed in U.S. Pat. No. 5,057,540. Use of 3D-MPL is described by Ribi et al. in Microbioloa (1986) Levie et al.(eds) Amer. Soc. Microbiol. Wash. D.C., 9–13. Use of Quil A is disclosed by Dalsgaard et. al.,(1977), Acta Vet Scand, 18, 349. Use of combined 3D-MPL and QS21 is described in WO 94/00153 (SmithKline Beecham Biologicals s.a).

As a further exemplary alternative, the proteins can be encapsulated within microparticles such as liposomes or associated with oil-in-water emulsions. Encapsulation within liposomes is described by Fullerton in U.S. Pat. No. 4,235.877. In yet another exemplary alternative, the proteins can be conjugated to an immunostimulating macromolecule, such as killed Bordetella or a tetanus toxoid. Conjugation of proteins to macromolecules is disclosed, for example by Likhite in U.S. Pat. No. 4.372,945 and Armor et al. in U.S. Pat. No. 4,474,757.

The amount of the protein of the present invention present in each vaccine dose is selected as an amount which induces an immunoprotective response without significant, adverse side effects in typical vaccines. Such amount will vary depending upon which specific immunogen is employed and whether or not the vaccine is adjuvanted. Generally, it is expected that each dose will comprise 1–1000 μg of protein, preferably 1–200 μg. An optimal amount for a particular vaccine can be ascertained by standard studies involving observation of antibody titres and other responses in subjects.

In order to define the invention more clearly reference is made to the appended drawings, in which:

FIG. 1 shows the construction scheme for chimeric gB.

Figure 2:
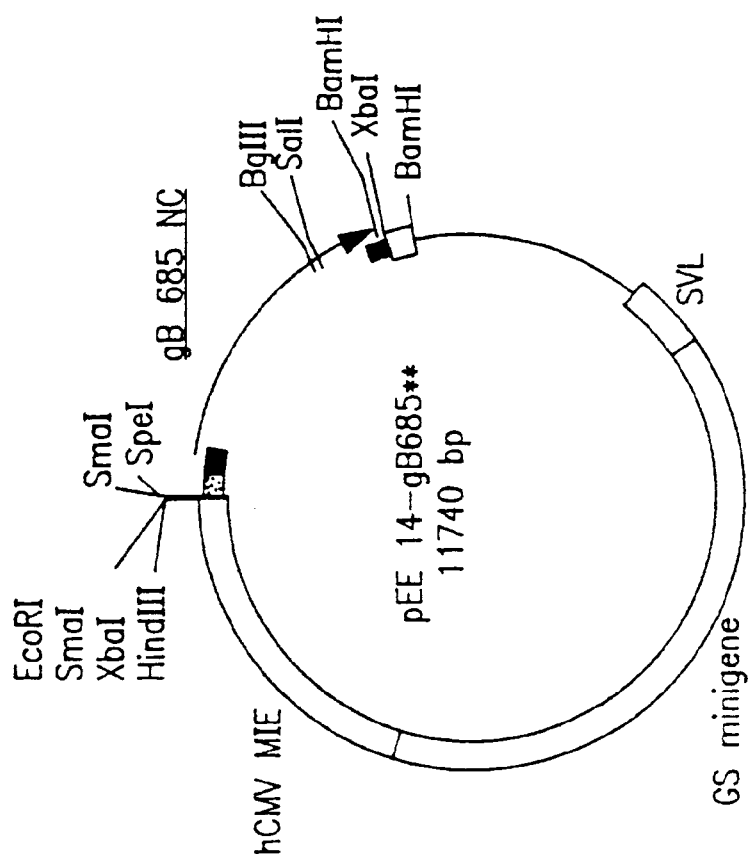
FIG. 2 shows a plasmid map of pEE14-gB685**

The invention will now be illustrated by reference to the following examples.

EXAMPLE 1

Construction of Chimeric gB Molecules

The following construction steps were performed in order to create the different gD/gB fusion molecules (chimeric $gB_{685}$* and chimeric $gB_{685}$**), see FIG. 1.

a) $gB_{685}$ NC (Non Cleavable)

To generate pUC12-gB685, the gB gene of strain AD169 HCMV was subcloned from the genomic Hind III F fragment as an Ecl 1 fragment into the Sma 1 site of pUC12 (Yanisch-Perron, C et al 1985 GENE 33, 103). A stopcodon and BamHI site was inserted into the internal EcoR1 site (position 2208 of AD 169 gB) generating a truncation at aminoacid 685 (ie lacking the transmembrane anchor [aminoacids 712–776]). The HCMV gB sequence is known from Cranage et al Embo J. 1986, 5,3057–3063.

In order to obtain more secretion of truncated $gB_{685}$ antigen into the cell culture supernatant of CHO-K1 cells we introduced first in the previously cloned and truncated $gB_{685}$ plasmid construct. pUC12-$gB_{685}$ (pM7) also named pRIT14224, a double mutation rendering the gB cleavage site at 459/460 (AD169 strain) non-cleavable. This was accomplished by exchanging (PCR) Arg458 and Arg459 for Glutamine and Threonine respectively. More specifically the $gB_{685}$ NC (non cleavable) plasmid construct was generated by recombinant PCR (RPCR) according to a method described in ref. 1. Therefore two DNA plasmid preparations of pUC12-$gB_{685}$ were digested respectively by HindIII and XmnI. Both linearised plasmids were separately amplified by PCR (Ampli Taq) using respectively primer couples Dir 268, Dir 269 and Dir 270. Dir 271. The amplified products, about 10 ng of each PCR reaction were mixed together and competent E. coli HB101 cells were transformed.

Thanks to the created homologous ends (respectively 75 nct for the pUC-region and 13 nct for the mutated gB region) the linear PCR products can undergo circularisation by recombination in vivo. About 30% of the obtained clones (0,15% efficiency) were without errors after sequencing the whole gB region. One E. coli clone pUC12-$gB_{685}$ NC also named pRIT14225 was chosen and DNA was prepared. A BamnHI fragment of 2200 bp containing the $gB_{685}$ NC cassette was gel purified and ligated into the expression vector pEE14 cut by BclI. The resulting recombinant plasmid is pEE14 $gB_{685}$ NC as named pRIT14226 or pC2 (see FIG. 1b).

(1) Jones D. H. and S. C. Winistorfer 1992 Biotechniques 12:528–533.

b) gD/gB Fusion Protein (Chimeric $gB_{685}$*)

Construct $gB_{685}$* was created as follows (see FIG. 1c). The 5' leader sequence (86 bp) and signal sequence (aa1 to 25) of glycoprotein gD of HSV2 and the mature sequence of gD from aminoacids 26 to 52 was fused to aminoacid 28 of mature HCMV gB (minus 3 aminoacids). The construction steps were as follows: an EcoRI-PvuII (240 bp) gD2 fragment derived from plasmid pEE14-gD2t 1A also named pRIT13832 was ligated to a 1980 bp ScaI/BamHI fragment from pUC12-$gB_{685}$ in the presence of the pEE14 vector out by EcoRI/BclI. This resulted in pEE14-$gB_{685}$* also named pRIT14227 or pC3. The obtained chimeric gB expression cassette was verified by automated DNA sequencing.

Plasmid pEE14-gD2t 1A contains a truncated gD coding sequence (HSV2 strain G) from aminoacids 1→309 in a CHOK1 vector pEE14 (ref. 3) under the control of the major immediate early promoter of human cytomezalovirus (hCMV-MIE). The HSV2 gD sequence is known from Lasky et al, DNA, 1984, 3, 23–29.

c) Chimeric $gB_{685}$**

The $gB_{685}$** construct (see FIG. 1d) was created by adding at the C-end of the above mentioned chimeric $gB_{685}$* expression module, an extension of 12 aminoacids (PEDSALLEDPED) derived from an internally gD2 sequence (i.e. same truncated C-end of gD2t molecule which happens to be very well secreted in CHO-K 1 cells). More particularly the following construction steps were performed. A 2002 bp long HindIII/BglII fragment from pEE14.$gB_{685}$* (pRIT14227) was ligated with a 285 bp BglIII/XbaI fragment (generated by PCR using primers Dir 287 and Dir 288 on pUC122-$B_{685}$ NC) together with vector pEE14 cut by HindIII/XbaI. The resulting plasmid is pEE14-$gB_{685}$ also named pRIT14229 or pC4 (see FIG. 2). After sequencing the 3' end of the $gB_{685}$ cassette of 10 clones, clone # 30 was chosen and DNA was prepared by CsCl gradient purification.

EXAMPLE 2

Expression in Eukaryotic Cells a) Expression in CHO Cells

CHO-K1 cells were transfected classically by the Ca-phosphate method using respectively 20 µg DNA of the following expression plasmids, pEE14-$gB_{685}$ NC. pEE14-$gB_{685}$* and pEE14-$gB_{685}$**. Selection of stable transformant clones was done in GMEM medium, 10% dialysed FBS lacking glutamine (see ref. 3). The selection method for glutamine synthetase gene expression of pEE14 vector (Celltech) relies on the ability of the transfected plasmid DNA to confer resistance to a low level of methionine sulfoximine (MSX). CHO-K1 clones were isolated by cloning cylinders (±26 clones respectively for $gB_{685}$ NC and $gB_{685}$* construct). CHO-K1 $gB_{685}$ transfectant clones were selected/isolated using a different protocol. After transfection (Ca-phosphate) of about 1,4 & $10^6$ cells in F80 $cm^2$ T-flask, the cells were distributed into 4×96 well plates and each well was seeded with ±3500 cells. After selection for about 2–3 weeks a total of 25 clones was obtained. Six clones were further amplified in F25 $cm^2$ and tested by Western blot analysis using α-gD (mAb 4846) antibody and tested also by gB-specific Elisa (1F10G2/LCT62). Five out of six clones secreted high levels of chimeric $gB_{685}$ protein into the culture supernatant of CHO-K1 cells.

These CHO-K1 clones were amplified and cell vials were made. Clone pC4204.20 was chosen for further characterisation. Expression level of $2B_{685}$** antigen secreted into culture supernatant was estimated at 3–4 µg/ml/$5.10^5$ cells by Western blot (mAb 4846) analysis using purified gD2t as reference.

Table I shows the results of the expression characterisation studies performed by radioimmunoprecipitationassay (RIPA) on CHO-K1 cells expressing respectively $gB_{685}$. $gB_{685}$ NC. $gB_{685}$* and $gB_{685}$** antigens. Cell extracts and culture supernatants were inununoprecipitated using a panel of different monoclonal antibodies (W. Britt) directed against gB HCMV (one sequential mAb 27-156 and two conformational mAb's 27-39 and mAb 9-3) and a neutralising human α-CMV serum (#243) and by a sequential monoclonal antibody (mAb 4846) directed against the NH2-part (aa12 to 23) of HSV2 gD.

Table II shows the Western blot results using the same monoclonal antibodies and human a-CMV serum (#243). Above results suggest that the chimeric $gB_{685}$** antigen display an enhanced secretion capacity with respect to the previously analysed $gB_{685}$ antigen derived from CHO-K1 $gB_{685}$ (clone 44). The above results suggest also that $gB_{685}*$, $gB_{685}$ and also $gB_{685}$ NC—but not or to a much lesser degree $gB_{685}$—are secreted and are found in a conformational state, well recognised by conformational antibodies and human neutralising CMV serum (#243). The chimeric $gB_{685}$ and $gB_{685}$ NC expressed antigen may have a conformation that closely resembles that of native gB and may thus be extremely useful for development of a HCMV vaccine. It might be encouraged also to use the chimeric $gB_{685}**$ immunogen as a component of a HSV gD vaccine. This because it was shown by Watari et al. 1987 (2) (and references therein) that aal to 23 of mature gD2 contains a CTL epitope and could elicit a neutralising and protective immune response in mice model.

Although not a preferred embodiment of this invention, the use of these chimeric $gB_{685}*$ one $gB_{685}**$ antigens could facilitate isolation/purification via "gD-tag" by immunoaffinity chromatography (as was recently shown by us).

It should be noticed that all expressed non cleavable CHO-K1 $gB_{685}$ constructs in spite of the presence of the mutated 458/459 aminoacids—display a (small) protein band at 33–35 kD (resembling to the gp33 part of $gB_{685}$ cleavable). This band is recognised in cell extracts by WB analysis using nAb 27-156 ($\alpha$-gp33). This finding suggests strongly that an alternative nearby cleavage site is activated in these non cleavable recombinant $gB_{685}$ constructs.

It should also be stressed that we have found a non-described (yet) processing event i.e. processing site in the NH2-part of the gB molecule (gp92-116). The detection was made possible due to the added gD-tag at the aminoterminal part of the $gB_{685}$ module. A 34–36 kD band was detected in cell extracts by WB analysis using ($\alpha$-gD monoclonal antibody mAb4846. A 69–70 kD protein fragment most likely corresponding to the carboxy half of the gp92-116 part of gB was detected only by RIPA using gB specific mabs (suggesting co-precipitation with gp33-part), this same 69–70 kD band was also recognised by human neutralising anti CMV serum #243 in RIPA (see also table I). This 69–70 kD band has been detected in retrospect in all CHO-K1 gB constructs (cleavable or not). This cleavage of the aminoterminal part of gB (gp92-116) might be of biological relevance (fusion) and this finding might be important for vaccine development.

(2) J. Exp. Med. 1987, 165:459–470.
(3) Cockett, M. I. Bebbington, C. R. and Yarranton, G. T. 1990 Biotechnology 8 662–667.

EXAMPLE 4

Enhancing gB Gene Expression with Sodium Butyrate or DMSO

Sodium butyrate (Na But) was added at different concentration (0.5 mM, 1 mM, 2 mM, 3mM, 4 mM, 5 mM, 10 mM) to cultures of CHOK1 gB subclones. A clear effect was observed (WB-analysis, mAb 4846) starting from 0.5 mM NgBut on, with maximum expression levels achieved at 2 mM–4 mM NgBut. At higher (5 mM) concentration (more expression per cell is observed) the cytostatic effect of NgBut is too pronounced and therefore the total yield of gB is not much increased versus 2 mM NaBut treatment. Typical results for a subclone of gB were about 16 fold enhancement of basal gene expression of gB (WB-analysis) when 2mM NgBut was added and when gB** was accumulated during 4 days. With DMSO added at 2% an 8–12 fold increase was observed.

TABLE 1

Summary of the Radioimmunoprecipitation (RIPA) results on different CHO-K1 cell lines expressing different recombinant $gB_{685}$ antigens. Cell lysates were made in RIPA-buffer and cell culture supernatants (SN) were analysed with a panel of different monoclonal antibodies directed against gB and a neutralizing human $\alpha$-CMV serum # 243.

|  | mAb27.156 | mAb27.39 | mAb9.3 | mAb48.46 | hû CMV serum # 243 |
|---|---|---|---|---|---|
| gB685 Cells: |  |  |  |  |  |
| 110 kD | + | + | + | − | + |
| 82 kD | ± | ± | ± | − | ± |
| 69–70 kD | +++ | +++ | ++++ | − | +++ |
| 33–35 kD | +++ | +++ | ++++ | − | +++ |
| SN: | + | + | − | − | ± |
| 120–125 kD |  |  |  |  |  |
| gB685NC Cells: |  |  |  |  |  |
| 110 kD | ++ | ++ | +++ | − | ++(+) |
| 69–70 kD | + | + | ++ | − | ++ |
| 33–35 kD | + | + | ++ | − | ++ |
| SN: | +++ | ++++ | ++++ | − | ++++ |
| 120–125 kD |  |  |  |  |  |
| gB685* Cells: |  |  |  |  |  |
| 115 kD | + | − | + | + | + |
| 69–70 kD | + | + | + | − | + |
| 33–35 kD | + | + | + | + | + |
| SN: 130 kD | + | + | + | + | ± |
| gB685** Cells: |  |  |  |  |  |
| 125 kD | ++++ | +++ | +++ | +++ | +++ |
| 69–70 kD | +++ | ++ | +++ | − | ++ |
| 34–36 kD | +++ | ++ | +++ | − | ++ |
| SN: 130 kD | +++ | ++(+) | ± | ++++ | +++ |

TABLE II

Summary of the Western blot analyses performed with a panel of different monoclonal antibodies against gB and a neutralizing human $\alpha$-CMV serum # 243.

|  | mAb27.156 | mAb27.39 | mAb9.3 | mAb48.46 | hû CMV serum # 243 |
|---|---|---|---|---|---|
| gB685 Cells: |  |  |  |  |  |
| 110 kD | ++ | − | ++ | − | ± |
| 30–33 kD | ++ | − | +++ | − | − |
| SN: 120 kD | − | − | − | − | − |
| gB685NC Cells: |  |  |  |  |  |
| 110–115 kD | +++ | − | +++ | − | + |
| 30–33 kD | ++ | − | +++ | − | − |
| SN: 125 kD | ++ | − | ± | − | − |
| gB685* Cells: |  |  |  |  |  |
| 120 kD | + | − | ± | ++++ | − |
| 30–33 kD | ± | − | + | − | − |
| SN: 130 kD | ± | − | ± | +++ | − |
| gB685** Cells: |  |  |  |  |  |
| 125 kD | ++ | − | ++ | ++++ | − |
| 33–34 kD | ± | − | ++ | ++++ | − |
| SN: 130 kD | + | − | ± | ++++ | − |

TABLE III

Primer oligonucleotides and PCR conditions used to generate the different chimeric gB$_{685}$ constructs A) gB$_{685}$NC (non-cleavable)

Dir 268: 5' GGA CC<u>C</u> <u>A</u>AA <u>C</u>AA GTA CGA GTG (SEQ ID NO:1)

Dir 269: 5' CGC TGG TGA AAG TAA AAG ATG C (SEQ ID NO:2)

Dir 270: 5' GTA CTT GTT TGG GTC CTA TG (SEQ ID NO:3)

Dir 271: 5' CCG CTG TTG AGA TCC AGT TCG (SEQ ID NO:4)

PCR reaction conditions:
   on 0,5 µg HindIII or XmnI linearised pUC12-gB$_{685}$
     25 cycles: 2 min 94° C., 2 min 55° C., 2 min 72° C.
     1 cycle: 2 min 94° C., 2 min 55° C., 15 min 72° C.
   with primer couples Dir 268, Dir 269
   and separately with primer couples Dir 270, Dir 271

B) Chimeric gB$_{685}$**

Dir 287: 5' GCC TCA AGA TCT TCA TCG CCG GGA ACT CG 3' (SEQ ID NO:5)

```
                XbaI    Stop  D    E    P    D
   Dir 288: 5' T  AGC   TCT   AGA  TTA  ATC  CTC  GGG  ATC
   CTC  TAA  GAG  GGC  CGA  GTC  CTC  GGG  GGA  ATT  CGC 3' (SEQ ID NO:6)
   E    L    L    A    S    D    E    P              EcoRI (SEQ ID NO:7)
   ```

PCR: on 0,1 µg DNA of pUC12-gB$_{685}$ NC plasmid
     25 cycles: 2 min 95° C., 2 min 55° C., 2 min 72° C.
     followed by 2 min 95° C., 2 min 55° C. and 15 min 72° C.

---

What is claimed is:

1. A composition comprising:

an isolated fusion protein comprising a non-cleavable Human Cytomegalovirus glycoprotein B (HCMVgB) fused at its amino terminus to the carboxy terminus of a portion of Herpes simplex virus type 2 glycoprotein D (HSV2 gD), wherein said HCMV gB comprises amino acids 28–686 of the gB of HCMV strain AD 169 wherein arginine 458 and arginine 459 are replaced by glutamine and threonine, respectively and wherein said portion of HSV2 gD is selected from the group consisting of amino acids 1–52, amino acids 1–25 and amino acids 26–52; and a pharmaceutically acceptable carrier.

2. The composition as recited in claim 1 wherein said HCMV gB is further fused at its carboxy terminus to an internal HSV2 gD sequence comprising amino acids PEDSALLEDPED (SEQ ID NO: 8).

3. The composition as recited in claim 1 wherein said composition further comprises an adjuvant.

4. The composition as recited in claim 2 wherein said composition further comprises an adjuvant.

5. The composition as recited in claim 3 wherein said adjuvant is selected from the group consisting of 3-deacylated monophosphoryl lipid A (3D-MPL), QS-21 and a mixture thereof.

6. The composition as recited in claim 1 wherein said carrier is an oil-in-water emulsion.

7. A method of inducing immunogenicity comprising:

administering to a patient in need thereof an effective amount of a composition comprising a pharmaceutically acceptable diluent or carrier and a fusion protein comprising a non-cleavable Human Cytomegalovirus glycoprotein B (HCMV gB) fused at its amino terminus to the carboxy terminus of a portion of Herpes simplex virus type 2 glycoprotein D (HSV2 gD), wherein said HCMV gB comprises amino acids 28–686 of the gB of HCMV strain AD 169 wherein arginine 458 and arginine 459 are replaced by glutamine and threonine, respectively and wherein said portion of HSV2 gD is selected from the group consisting of amino acids 1–52, amino acids 1–25 and amino acids 26–52.

8. The method as recited in claim 7 wherein said HCMV gB is further fused at its carboxy terminus to an internal HSV2 gD sequence comprising amino acids PEDSALLEDPED (SEQ ID NO: 8).

9. The composition as recited in claim 4 wherein said adjuvant is selected from the group consisting of 3-deacylated monophosphoryl lipid A (3D-MPL), QS-21 and a mixture thereof.

10. The composition as recited in claim 2 wherein said carrier is an oil-in-water emulsion.

11. The method as recited in claim 7 wherein said composition further comprises an adjuvant.

12. The method as recited in claim 11 wherein said adjuvant is selected from the group consisting of 3-deacylated monophosphoryl lipid A (3D-MPL), QS-21 and a mixture thereof.

13. The method as recited in claim 7 wherein said carrier is an oil-in-water emulsion.

* * * * *